United States Patent [19]

Dutcher et al.

[11] 4,209,019
[45] Jun. 24, 1980

[54] STYLET INSERTION GUIDE AND ROTATION CONTROL DEVICE FOR USE WITH BODY IMPLANTABLE LEAD

[75] Inventors: Robert G. Dutcher, Columbia Heights; Edward G. O'Neil, St. Paul, both of Minn.

[73] Assignee: Medtronic, Inc., Minneapolis, Minn.

[21] Appl. No.: 1,201

[22] Filed: Jan. 5, 1979

[51] Int. Cl.² .............................................. A61N 1/00
[52] U.S. Cl. .................. 128/419 P; 128/784; 128/DIG. 9
[58] Field of Search ............... 128/348, 419 P, 784, 128/786, 642, 656–658, 772, DIG. 9, 311, 312; 116/315

[56] References Cited

U.S. PATENT DOCUMENTS

| | | | |
|---|---|---|---|
| 3,974,834 | 8/1976 | Kane | 128/419 P |
| 3,991,762 | 11/1976 | Radford | 128/DIG. 9 |
| 4,027,678 | 6/1977 | Van Oostveen et al. | 128/419 P |
| 4,086,715 | 5/1978 | Bloniggn | 116/315 |
| 4,106,512 | 8/1978 | Bisping | 128/419 P |

OTHER PUBLICATIONS

"Mechanical Engineering", Jan. 1967, p. 48.

*Primary Examiner*—William E. Kamm
*Attorney, Agent, or Firm*—Schroeder, Siegfried, Ryan, Vidas, Steffey & Arrett

[57] ABSTRACT

A body implantable lead and a stiffening stylet with a flexible tip for imparting rigidity to the lead to facilitate attachment of the lead to an internal body organ and for transmitting torque to the distal end of the lead. A flexible tip stiffening stylet is provided for insertion into a lumen in the lead extending from a pin at its proximal end along the length of the lead conductor to the electrode. At the proximal end of the stylet, a guide and rotation control device is provided to aid in insertion of the lead and stylet and to facilitate rotation of the stylet to permanently attach the electrode at the distal end to a body organ through endothelial tissue.

5 Claims, 5 Drawing Figures

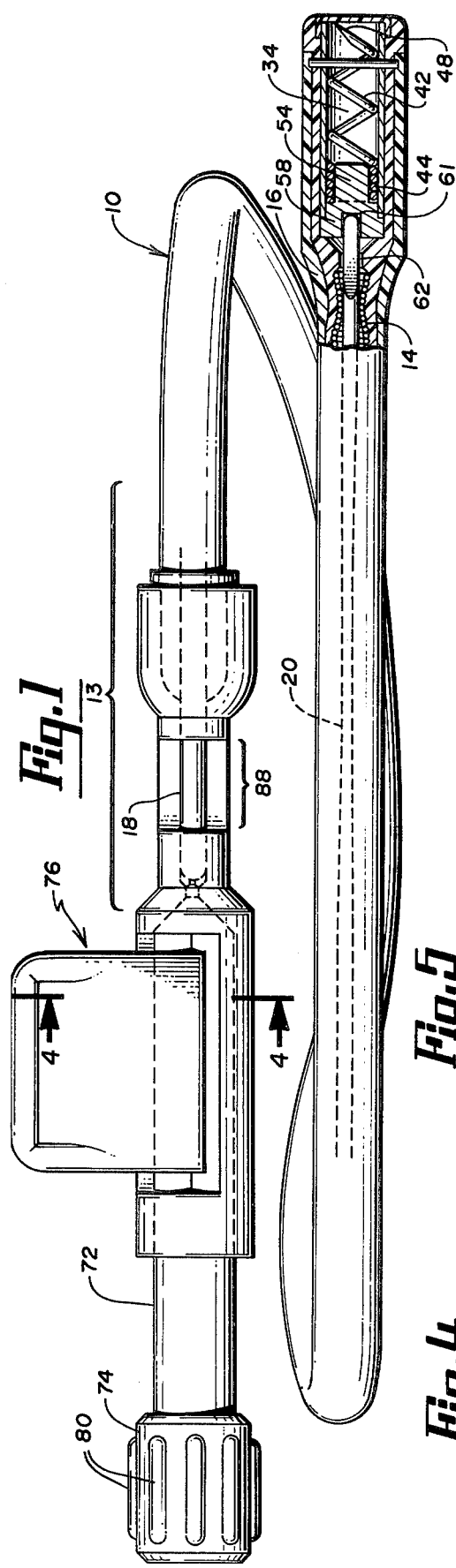
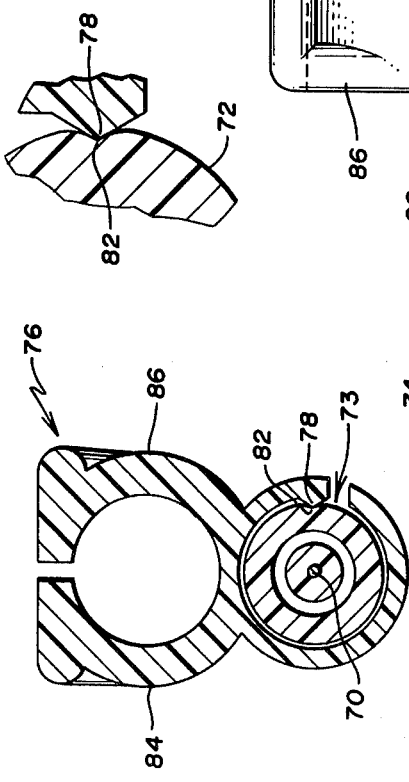
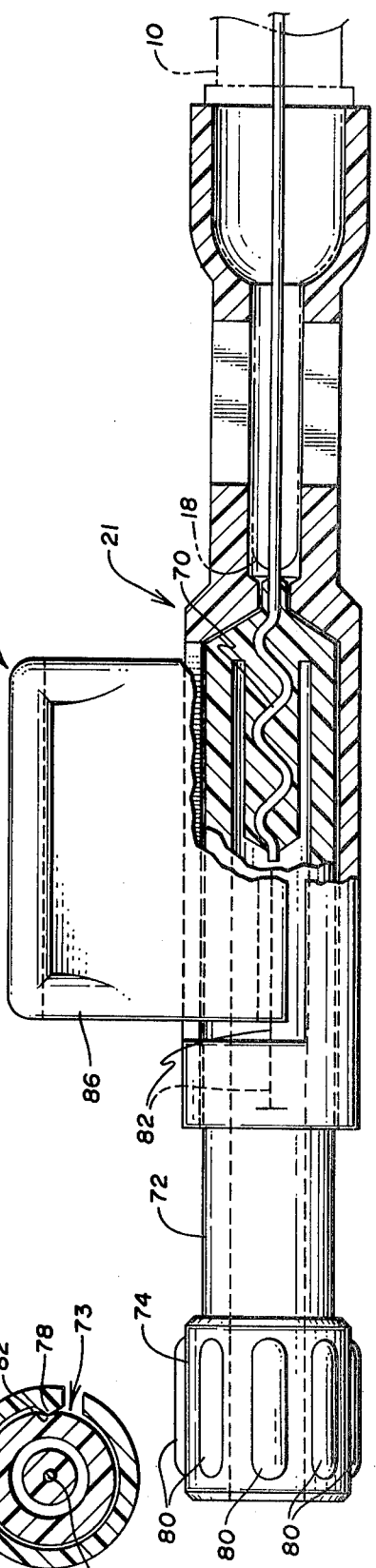

STYLET INSERTION GUIDE AND ROTATION CONTROL DEVICE FOR USE WITH BODY IMPLANTABLE LEAD

DESCRIPTION

Background of the Invention

This invention relates to a stylet insertion guide for use with a lead bearing an electrode for electrically connecting an organ inside a living animal body to an electrical device. Notwithstanding its various uses, this invention will be described for use as an endocardial pacing and sensing lead for connecting an artificial cardiac pacemaker to cardiac tissue.

Endocardial pacing and sensing leads of the type shown in United States patent application Ser. No. 839,062, filed Oct. 3, 1977, and now abandoned and replaced by a continuation application 6,620, filed Jan. 26, 1979, for a Body Implantable Lead With Protected Extendable Tissue Securing Means, for example, comprise one or more lengths of hollow, coiled wire conductor encased within a suitable insulating material such as silicon rubber, that is substantially inert to body fluids and tissues, a hollow connector pin attached to the proximal end of each of the conductors, and an electrically conductive electrode at the distal end of each of the conductors adapted to be placed in contact with the endocardium of the patient. A lumen extends through each pin and the corresponding lengths of coiled wire conductor to the electrode at the distal ends thereof and receives a stiffening stylet of cylindrical corrosion resistant wire for imparting stiffness to the lead to facilitate its advancement through the venous system of the patient and into the apex of the right ventricle. With the stylet removed from the lead, the lead is very flexible and difficult to so advance. Further details of the construction and utility of such endocardial pacing leads may be obtained by reference to U.S. Pat. Nos. 3,348,548 and 4,046,151, as well as the above-identified abandoned and replaced by a continuation application 6,620, filed Jan. 26, 2979 application Ser. No. 839,062.

An improved cardiac pacing lead employing a rigid helix with a sharp tipped distal end adapted to be screwed into the endocardium is disclosed in co-pending U.S. Pat. application 839,062, now abandoned and replaced by a continuation application 6,620, filed Jan. 26, 1979 which is assigned to Medtronic, Inc. The improved lead disclosed in that application can be lodged in and permanently secured to or removed from body tissue without the use of bulky sleeves or catheter introducers to protect the patient's veins and tricuspid valve from snagging on the sharp tip of the helix.

In the improved lead disclosed in Ser. No. 839,062, now abandoned, and replaced by a continuation application 6,620, filed [26, 1979 the tissue securing means is a helix with a piston member fixed to its proximal end and positioned in a chamber within the electrode body. A stylet having a molded knob with an extended shaft at its proximal end is passed through a lumen in the lead which communicates with the opening in the proximal end of the lead body such that the distal end of the stylet which is shaped in the form of a screwdriver head, is engagable with a slot in the head of the piston means. The stylet may be rotated after the distal end of the lead is positioned near the endocardial tissue and when the stylet is rotated the piston means is caused to advance the helix out of the distal opening in the electrode lead by screw action and into the endocardial and myocardial tissue to secure the electrode.

The implantable lead of the present invention incorporates an improved stylet guide and rotational control to increase the effectiveness in the placement of either the endocardial leads of the type disclosed in U.S. Pat. No. 4,046,151 or in the co-pending application Ser. No. 839,062, now abandoned and replaced by a continuation application 6,620, filed Jan. 26, 1979. A feature of the present invention is the provision of a stylet guide and rotational control device useful for a controlled insertion of the helical tissue securing means into body tissue by a determinable number of turns in an efficient and controllable manner.

SUMMARY OF THE INVENTION

The above features and advantages of the present invention, as well as others, are accomplished by providing a body implantable lead of the type having a lumen for receiving a stiffening stylet extending through the connector pin of the lead at its proximal end, through the length of the lead and to the electrode at the distal end thereof with stiffening stylet having a flexible tip at its distal end and a knob with an extended shaft at its proximal end.

The operation of the lead and stylet is enhanced by utilizing an improved guide and rotation control device to permit selective rotation of the stylet knob and shaft to insert the helical tip. The rotation control device includes means for providing a perceivable indication to the operator for each 360 degrees rotation of the stylet knob and also includes detent means for preventing undesired rotation of the stylet. The rotation control device also includes a release means which permits the operator to release the stylet knob detent after the helix has been rotated the desired number of rotations to release the residual torque and to permit the stylet to be freely rotated a fractional turn. The rotation control device has a cut-away portion to permit ready access to the pin at the proximal end of the lead to permit electrical connection thereto using a clip lead.

Other features, advantages, and objects of the present invention will hereinafter become more fully apparent from the following description of the drawings, which illustrate the invention.

BRIEF DESCRIPTION OF THE DRAWINGS

FIG. 1 is a view of a preferred embodiment of the body implantable lead of the present invention;

FIG. 3 is an enlarged view of the rotation control device shown in FIG. 1 partially cut away to show constructional details;

FIG. 4 is an end view of the mechanism of FIG. 3; and

FIG. 5 is an enlarged view of the mechanism shown in FIG. 4 to show the detent feature more clearly.

DESCRIPTION OF THE PREFERRED EMBODIMENT

Figure 2:
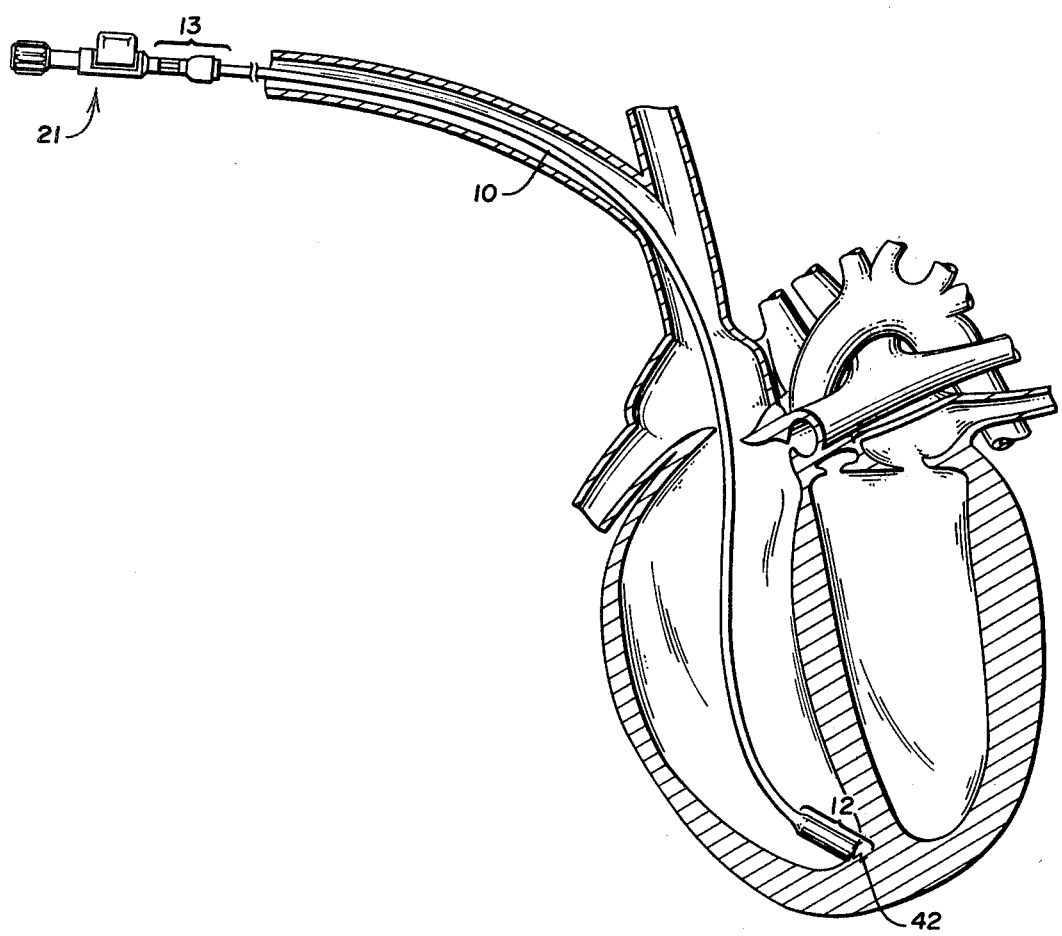
FIG. 2 shows the lead of FIG. 1 being lodged in and permanently secured to the tissue forming the apex of the right ventricle of the heart.

Referring now to the preferred embodiment of the invention depicted in FIG. 1, there is shown an intravascular endocardial lead comprising an elongated lead 10, a distal electrode end portion 12, and a proximal terminal end portion 13. The lead, in unipolar configuration, comprises a closely wound, coiled conductor 14 in the form of a spring spirally wound about and along the axis of the conductor. The spring coil 14 extends through the length of lead 10 in a lumen of a jacket or sleeve 16 of electrically insulating material.

The structure and operation of the distal end portion 12 of lead 10 are discussed in detail in co-pending application Ser. No. 839,062, now abandoned, and replaced by a continuation application 6.620, filed Jan. 26, 1979 and the reference characters used in that application have been carried over to the present application where appropriate. As more fully described in that application, a tissue securing member in the form of a relatively rigid circular corkscrew or helix 42 is provided having a proximal end 44 of several closely wound turns located in the chamber 34 toward the proximal end thereof. Helix 42 has a sharpened tip 48.

The stylet used in the preferred embodiment of the invention disclosed herein is disclosed in a co-pending application entitled Flexible Tip Stiffening Stylet For Use With Body Implantable Lead filed on the same date as the present application. The corrosion resistant stylet disclosed therein has a reduced diameter portion near the distal end to facilitate transmission of the rotational torque by the stylet in situations where the stylet and lead assembly are sharply bent in the vicinity of the distal end of the lead.

If the above described flexible tip stylet is to be used to lodge the helix into the body tissue, it may be necessary to utilize a standard uniform diameter stylet to stiffen the lead to facilitate insertion of the lead through the venous system and into the chamber of the heart where the helix 42 is desired to be implanted. After the lead is inserted and positioned, the insertion stylet is removed and the flexible tip stylet may then be inserted and utilized for the remainder of the implanting process. FIG. 2 shows the lead and stylet positioned for insertion of the helix in the apex of the right ventricle of the heart.

As indicated in co-pending application Ser. No. 839,062, now abandoned and replaced by a continuation application 6.620, filed Jan. 26, 1979, there is also provided in chamber 34 at the distal end of lead 10, a member 54 which takes the form of a piston having a generally circular cross section and has a proximal end at which is located a slotted head 58 and a distal end portion 60 which is somewhat smaller in cross sectional diameter than head 58. Head 58 has a slot 61 in the proximal end thereof and is adapted to receive the distal end of stylet 20 which terminates at its distal end in a screwdriver tip 62. When flexible tipped stylet 20 is fully inserted into lead 10 through pin 18, its screwdriver tip portion 62 is firmly seated in slot 61.

Turning now to the insertion tool 21, which is shown mounted on the proximal end portion of lead 10 and is shown in enlarged and partially cut away form in FIG. 3, the proximal end 70 of stylet 20 is bent into a zig-zag portion which assures that stylet 20 is permanently lodged in molded shaft 72 and is positioned such that stylet 20 exists from shaft 72 along its axis. In the preferred embodiment shown, the proximal end of stylet 20 has a diameter of 0.0159 inches and the radii of the bends of the proximal end 70 of stylet 20 are approximately 0.020 inches, while the "amplitude" of the zig-zag portion is approximately 0.060 inches. Shaft 72 has at its proximal end a molded knob portion 74 which has a plurality of projections 80 from its surface to facilitate gripping of the knob and to permit its easy rotation. The insertion tool is molded from acetal resin in the preferred embodiment shown.

Rotation of knob 74 and shaft 72 directly transmits rotational torque to stylet 20. The screwdriver blade tip 62 of stylet 20 engages slot 61 in piston 54 and in turn rotates the pointed tip 48 of the helix 42 of the lead to advance it into the body tissue against which the distal end of the lead was positioned when the rotation of helix 42 was commenced.

Shaft 72 is shown in FIGS. 1 and 3 inserted in a guide and ratchet portion 76. As shown in FIG. 4 and the enlarged view in FIG. 5, the guide and ratchet portion 76 has a circular cross section guide chamber 73 therein through which shaft 72 projects. A portion of chamber 73 is molded with a tooth or pawl 78 which, when shaft 72 is inserted in guide 76, bears upon the surface of shaft 72. The surface of shaft 72 has a longitudinal slot or notch 82 along the axis of shaft 72 which is engaged by tooth 78 of guide 76 when slot 82 is rotationally aligned with notched tooth 78. The relative dimensions of the shaft 72 and the ratchet and guide portion 76 are such that there is a positive tracking force exerted by tooth 78 on the surface of shaft 72 as it is rotated. The depths of notch 82 and the shape of tooth 78 assure that a welldefined snap action is provided when the notch 82 is aligned with tooth 78 upon rotation of the shaft. In addition to providing a tactile indication to the operator that a particular point in rotation has been reached, a detent action of tooth 78 and notch 82 restrains inadvertent further rotation of the stylet in either rotational direction. If the operator desires to release the detent, the upper projecting "ear" portions 84 and 86 can be squeezed together to bend the guide to distort the chamber in which shaft 72 is positioned to remove tooth 78 from engagement with notch 82.

In summary, lead 10 may be positioned in the appropriate position in the heart using a conventional stylet which is then removed. After the lead is positioned, the insertion tool 21 is mounted thereon, stylet 20 as described herein is inserted through the tool 21 and into lead 10, and screwdriver tip 62 of stylet 20 engages slot 61 of piston 58. The shaft 72 is then inserted into guide chamber 73 of guide 76. Handle 74 is then rotated in the correct direction to cause helix 42 to advance into the tissue against which the distal end of lead 10 was placed. A distinct click is produced upon each full rotation of shaft 72 by the interaction of pawl 78 and notch 82 of the insertion tool and undesirable backlash or reverse rotation of the shaft is avoided by the detent action of pawl 78 and notch 82. After insertion is believed complete and the desired number of rotations have been counted, the ears 84 and 86 of insertion tool 21 are squeezed together and the detent released to release residual torque and the knob rotated one-half turn while noting the degree of rotation resistance encountered. If the lead is adequately fixed, one may feel an increasing resistance while rotating the stylet. If the helix is properly lodged in the tissue of the organ, it can also be confirmed to move with the heart when viewed on a fluoroscope. The lead can also be lightly pulled while the fluoroscope is monitored to confirm that the helix continues to beat with the heart indicating that the helix 42 is firmly implanted.

The cut away portion 88 of insertion tool 21 permits access to pin 18 of lead 10 during insertion and while the stylet is being rotated so that electrical measurements may be made or stimulation can be applied without removal of the stylet and its insertion tool.

Although a unipolar lead design has been illustrated in the description of the preferred embodiment, it will be understood that bipolar leads (that is a lead carrying two electrodes and conductors) may as readily utilize the novel structure of the present invention. It should be understood that although the use of the lead 10 has been described for use in a cardiac pacing system, lead 10 could as well be applied to other types of body stimulating systems.

It should be further understood, of course, that the foregoing disclosure relates only to the best mode known to the inventors of many possible modes of practicing the invention and that numerous modifications may be made therein without departing from the spirit and scope of the invention as set forth in the appended claims.

We claim:

1. A stylet assembly for use in a body-implantable lead adapted to be connected at its proximal end to a medical device and secured at its distal end to tissue of a living body for electrical stimulation thereof and for detecting electrical signals, with said lead comprising;
    an electrical conductor extending between the proximal and distal ends of said lead;
    electrode head means affixed to the distal end of said lead having electrode means exposed to body tissue and electrically connected to the distal end of said conductor and adapted to supply electrical impulses to and receive electrical signals from tissue at a desired location inside the living body, said electrode head means having a chamber therein;
    a lumen extending from the proximal end of said lead to said chamber;
    material means substantially inert to body fluids and tissue encasing said conductor and said lumen;
    helical tissue securing means extending axially from the distal end of said lead adapted to be screwed into body tissue;
    rotatable means within said chamber coupled with said helical tissue securing means and adapted to be rotated to in turn rotate said helical tissue securing means to extend it from said chamber and into body tissue;
    said stylet assembly comprising in combination:
        stylet means adapted to extend through said lumen and engage said rotatable means;
        knob means extending from the proximal end of said stylet means for rotating said stylet and said rotatable means to advance said helical tissue securing means from said retracted position within said chamber to said advanced position and into body tissue to secure said electrode means in contact with body tissue; and
        guide means constructed and arranged to receive said knob means, said guide means including index means providing an indication each time a predetermined rotational increment has been traversed.

2. The invention claimed in claim 1 wherein said index means comprises one or more longitudinal slots along said knob means and a pawl mounted on said guide means, said pawl being constructed and arranged to engage one or more of said slots as said knob means is rotated.

3. The invention claimed in claim 2 wherein said index means is constructed and arranged to provide a detent action and restrain rotational movement of said knob when said pawl engages one or more of said slots.

4. The invention claimed in claim 3 wherein the detent action of said index means may be released by release means constructed and arranged to remove said pawl from said slots.

5. The invention claimed in claim 1 wherein said guide means is constructed and arranged for attachment to the proximal end of said lead, and wherein further means are provided to permit electrical connection to be made to said electrical conductor when said guide means is attached to the proximal end of said lead.

* * * * *